(12) United States Patent
Cabibihan et al.

(10) Patent No.: US 12,383,161 B2
(45) Date of Patent: Aug. 12, 2025

(54) DEVICE FOR DETECTING CHALLENGING BEHAVIORS IN PEOPLE WITH AUTISM

(71) Applicant: QATAR UNIVERSITY, Doha (QA)

(72) Inventors: John-John Cabibihan, Doha (QA); Ahmad Yaser Alhaddad, Doha (QA); Ahmad Qadeib Alban, Doha (QA); Malek Ayesh, Doha (QA); Abdulaziz Khalid Al-Ali, Doha (QA); Kishor Kumar Sadasivuni, Doha (QA); Hussein Aly, Doha (QA)

(73) Assignee: QATAR UNIVERSITY, Doha (QA)

( * ) Notice: Subject to any disclaimer, the term of this patent is extended or adjusted under 35 U.S.C. 154(b) by 0 days.

(21) Appl. No.: 18/141,174

(22) Filed: Apr. 28, 2023

(65) Prior Publication Data

US 2023/0363668 A1    Nov. 16, 2023

Related U.S. Application Data

(60) Provisional application No. 63/336,144, filed on Apr. 28, 2022.

(51) Int. Cl.
*A61B 5/11* (2006.01)
*A61B 5/00* (2006.01)
(Continued)

(52) U.S. Cl.
CPC .............. *A61B 5/11* (2013.01); *A61B 5/6801* (2013.01); *A63H 3/003* (2013.01); *G06F 3/015* (2013.01);
(Continued)

(58) Field of Classification Search
CPC ......... A61B 5/168; G16H 50/20; G16H 50/50
See application file for complete search history.

(56) References Cited

U.S. PATENT DOCUMENTS

| 11,298,071 | B1 * | 4/2022 | Saghafi | .................. A61B 5/725 |
| 2016/0180737 | A1 * | 6/2016 | Clark | ....................... G09B 5/02 434/236 |

(Continued)

OTHER PUBLICATIONS

T. Ploetz et al., "Automatic Assessment of Problem Behavior in Individuals with Developmental Disabilities", ResearchGate, https://www.researchgate.net/publication/235955673, Sep. 2012, 11 pages, DOI: 01.1145/2370216.2370276.

(Continued)

*Primary Examiner* — Peter R Egloff
(74) *Attorney, Agent, or Firm* — SQUIRE PATTON BOGGS (US) LLP

(57) ABSTRACT

A method may include establishing a connection with a wearable device and at least one sensory module device disposed within an environment. The method may also include receiving, from the at least one sensory module device, a recording of an auditory input from a subject and physical movement of the subject in the environment. The method may further include receiving, from the wearable device, at least one physiological signal of the subject. In addition, the method may include detecting, via machine learning, presence of a challenging behavior of the subject based on the received record of the auditory input, the physical movement, and the at least one physiological signal of the subject. Further, the method may include transmitting a notification of the detected challenging behavior to an external device.

12 Claims, 14 Drawing Sheets

(51) Int. Cl.
*A63H 3/00* (2006.01)
*G06F 3/01* (2006.01)
*G10L 25/63* (2013.01)
*A63H 3/28* (2006.01)

(52) U.S. Cl.
CPC .............. G10L 25/63 (2013.01); *A63H 3/28* (2013.01); *A63H 2200/00* (2013.01)

(56) References Cited

U.S. PATENT DOCUMENTS

| | | | |
|---|---|---|---|
| 2016/0358276 A1* | 12/2016 | Stephenson | G16H 20/00 |
| 2018/0358127 A1* | 12/2018 | Howsmon | C12Q 1/00 |
| 2019/0193280 A1* | 6/2019 | Mendelsohn | G16H 20/00 |
| 2020/0114521 A1* | 4/2020 | Mahoor | B25J 9/1697 |
| 2020/0406468 A1* | 12/2020 | Stoianovici | B25J 11/0005 |
| 2021/0236032 A1* | 8/2021 | Park | G06V 10/764 |
| 2022/0044823 A1* | 2/2022 | Hahn | G06F 18/2415 |
| 2023/0000423 A1* | 1/2023 | Sarkar | A61B 5/681 |

OTHER PUBLICATIONS

John-John Cabibihan et al., "Sensing Technologies for Autism Spectrum Disorder Screening and Intervention", Sensors 2017, 17, 25 pages.

\* cited by examiner

DEVICE FOR DETECTING CHALLENGING BEHAVIORS IN PEOPLE WITH AUTISM

CROSS-REFERENCE TO RELATED APPLICATIONS

This application claims priority from U.S. provisional patent application No. 63/336,144 filed on Apr. 28, 2022. The contents of this earlier filed application are hereby incorporated by reference in their entirety.

FIELD

Some example embodiments may generally relate to technologies to monitor the current state of a person. More specifically, certain example embodiments may relate to a device for detecting challenging behaviors in people with autism.

BACKGROUND

Globally, the number of children with autism is on the rise. Due to the rise of autism, trained staff in special needs centers and caregivers are unable to cope with the increased need to provide assistance to those with autism. A meltdown in autism may occur in 50% of those with autism spectrum disorder (ASD). Due to sensory overstimulation, meltdowns may be characterized by uncontrolled self-harming, throwing objects, and screaming, among others.

Children with autism exhibit challenging behaviors that interfere with their daily lives and affect their therapy sessions. Challenging behaviors may take on different forms such as obsession, withdrawal, repetitive behaviors, aggression, and tantrums. These behaviors may affect and potentially cause harm to the children themselves and others around them such as family members and other children. Parents, therapists, and caregivers face difficulty in reading the cues of a child's movements and, thus, often fail to anticipate the occurrence of a challenging behavior. Thus, there is a need to be able to detect such behaviors in an effort to de-escalate their intensities and prevent future occurrences. There is also a need for technology that can help in monitoring meltdown events in those with autism, and that can be used as a commercial product by parents and therapy centers to improve the services provided to children with autism.

SUMMARY

Some example embodiments may be directed to a method. The method may include establishing a connection with a wearable device and at least one sensory module device disposed within an environment. The method may also include receiving, from the at least one sensory module device, a recording of an auditory input from a subject and physical movement of the subject in the environment. The method may further include receiving, from the wearable device, at least one physiological signal of the subject. In addition, the method may include detecting, via machine learning, presence of a challenging behavior of the subject based on the received recording of the auditory input, the physical movement, and the at least one physiological signal of the subject. Further, the method may include transmitting a notification of the detected challenging behavior to an external device.

Other example embodiments may be directed to an apparatus. The apparatus may include at least one processor and at least one memory including computer program code. The at least one memory and computer program code may be configured to, with the at least one processor, cause the apparatus at least to establish a connection with a wearable device and at least one sensory module device disposed within an environment. The apparatus may also be caused to receive, from the at least one sensory module device, a recording of an auditory input from a subject and physical movement of the subject in the environment. The apparatus may further be caused to receive, from the wearable device, at least one physiological signal of the subject. In addition, the apparatus may be caused to detect, via machine learning, presence of a challenging behavior of the subject based on the received recording of the auditory input, the physical movement, and the at least one physiological signal of the subject. Further, the apparatus may be caused to transmit a notification of the detected challenging behavior to an external device.

Other example embodiments may be directed to an apparatus. The apparatus may include means for establishing a connection with a wearable device and at least one sensory module device disposed within an environment. The apparatus may also include means for receiving, from the at least one sensory module device, a recording of an auditory input from a subject and physical movement of the subject in the environment. In addition, the apparatus may include means for receiving, from the wearable device, at least one physiological signal of the subject. Further, the apparatus may include means for detecting, via machine learning, presence of a challenging behavior of the subject based on the received recording of the auditory input, the physical movement, and the at least one physiological signal of the subject. The apparatus may also include transmitting a notification of the detected challenging behavior to an external device.

In accordance with other example embodiments, a non-transitory computer readable medium may be encoded with instructions that may, when executed in hardware, perform a method establishing a connection with a wearable device and at least one sensory module device disposed within an environment. The method may also include receiving, from the at least one sensory module device, a recording of an auditory input from a subject and physical movement of the subject in the environment. The method may further include receiving, from the wearable device, at least one physiological signal of the subject. In addition, the method may include detecting, via machine learning, presence of a challenging behavior of the subject based on the received recording of the auditory input, the physical movement, and the at least one physiological signal of the subject. Further, the method may include transmitting a notification of the detected challenging behavior to an external device.

Other example embodiments may be directed to a computer program product that performs a method. The method may include establishing a connection with a wearable device and at least one sensory module device disposed within an environment. The method may also include receiving, from the at least one sensory module device, a recording of an auditory input from a subject and physical movement of the subject in the environment. The method may further include receiving, from the wearable device, at least one physiological signal of the subject. In addition, the method may include detecting, via machine learning, presence of a challenging behavior of the subject based on the received recording of the auditory input, the physical movement, and the at least one physiological signal of the subject. Further, the method may include transmitting a notification of the detected challenging behavior to an external device.

Other example embodiments may be directed to an apparatus that may include circuitry configured to establish a connection with a wearable device and at least one sensory module device disposed within an environment. The apparatus may also include circuitry configured to receive, from the at least one sensory module device, a recording of an auditory input from a subject and physical movement of the subject in the environment. The apparatus may further include circuitry configured to receive, from the wearable device, at least one physiological signal of the subject. In addition, the apparatus may include circuitry configured to detect, via machine learning, presence of a challenging behavior of the subject based on the received recording of the auditory input, the physical movement, and the at least one physiological signal of the subject. Further, the apparatus may include circuitry configured to transmit a notification of the detected challenging behavior to an external device.

BRIEF DESCRIPTION OF THE DRAWINGS

The accompanying drawings, which are included to provide a further understanding of the invention and are incorporated in and constitute a part of this specification, illustrate preferred embodiments of the invention and together with the detail description serve to explain the principles of the invention. In the drawings.

DETAILED DESCRIPTION

It will be readily understood that the components of certain example embodiments, as generally described and illustrated in the figures herein, may be arranged and designed in a wide variety of different configurations. The following is a detailed description of some embodiments of systems, methods, apparatuses, and/or computer program products for detecting challenging behaviors in people with autism.

The features, structures, or characteristics of example embodiments described throughout this specification may be combined in any suitable manner in one or more example embodiments. For example, the usage of the phrases "certain embodiments," "an example embodiment," "some embodiments," or other similar language, throughout this specification refers to the fact that a particular feature, structure, or characteristic described in connection with an embodiment may be included in at least one embodiment. Thus, appearances of the phrases "in certain embodiments," "an example embodiment," "in some embodiments," "in other embodiments," or other similar language, throughout this specification do not necessarily all refer to the same group of embodiments, and the described features, structures, or characteristics may be combined in any suitable manner in one or more example embodiments.

Additionally, if desired, the different functions or steps discussed below may be performed in a different order and/or concurrently with each other. Furthermore, if desired, one or more of the described functions or steps may be optional or may be combined. As such, the following description should be considered as merely illustrative of the principles and teachings of certain example embodiments, and not in limitation thereof.

Currently, there is no dedicated solutions to detect the occurrence of challenging behaviors among children with autism. In view of this and other drawbacks described above, certain example embodiments may provide sensor and wearable technologies may be used to monitor the current state of a person and subsequently improve the quality of life. The sensor and wearable technologies may provide a solution for detecting and monitoring challenging behaviors. For instance, the sensor and wearable technologies may help family members, therapists, and caregivers in taking precautionary measures to prevent an outburst before the child begins to show aggressive behaviors.

Figure 1A:
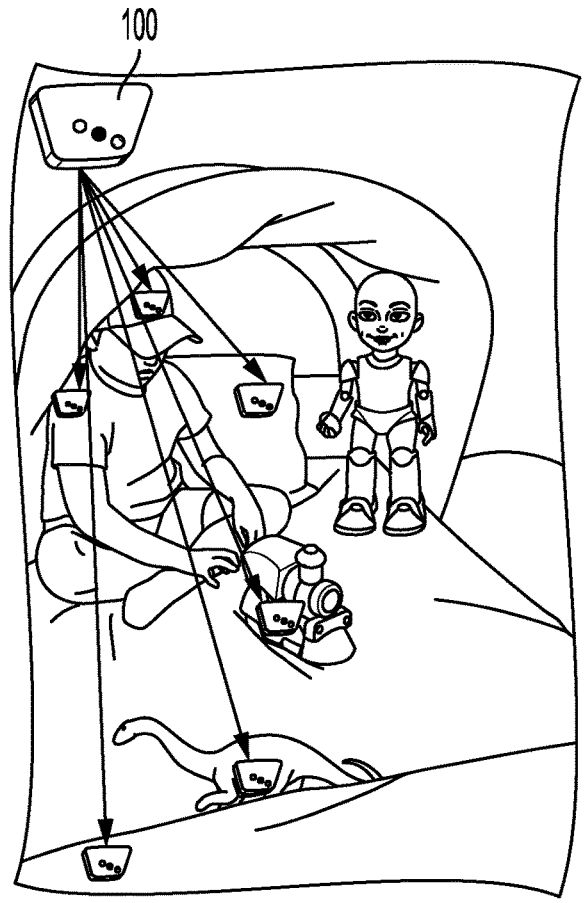
FIG. 1(a) illustrates an example environment where sensory modules may be disposed, according to certain example embodiments.
Figure 1B:
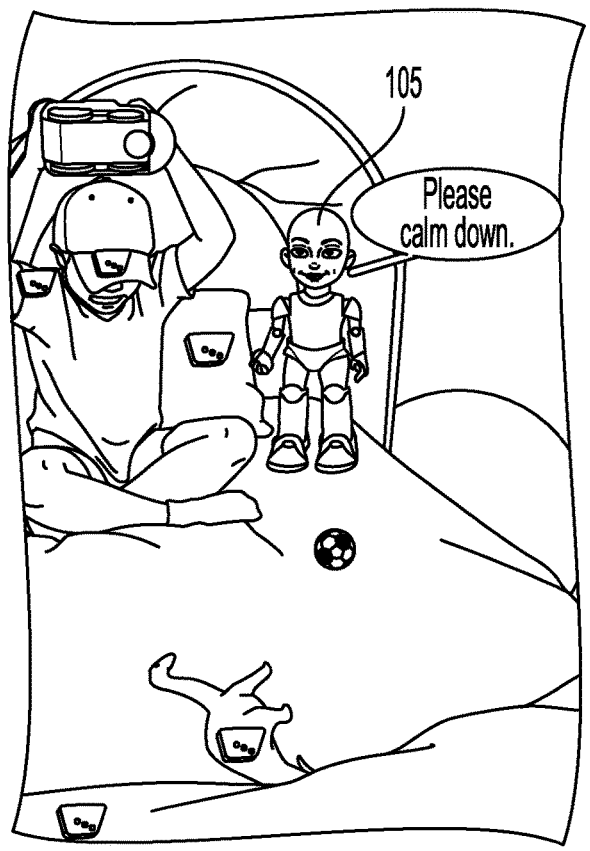
FIG. 1(b) illustrates an example environment with an interactive robot, according to certain example embodiments.

FIG. 1(a) illustrates an example environment where sensory modules may be disposed, according to certain example embodiments. FIG. 1(b) illustrates an example environment with an interactive robot, according to certain example embodiments. As illustrated in FIG. 1(a), sensory modules such as, for example, snap-on devices 100, may be placed at various locations in the environment. For instance, the snap-on devices 100 may be on a child's cap, shirt, pillow, blanket, and/or toys. Since the snap-on devices 100 may be distributed in multiple areas, the snap-on devices may acquire data from multiple sources to improve the detection of challenging behaviors. Although not illustrated in FIGS. 1(a) and 1(b), a wearable device may be provided to the child, and the wearable device along with the snap-on devices 100 may be wirelessly connected to a master device unit (MDU). As illustrated in FIG. 1(b), the environment may also include an interactive robot 105 which may be configured to emit encouraging messages when the snap-on devices 100 and/or the wearable device detects aggressive behaviors.

Figure 2:
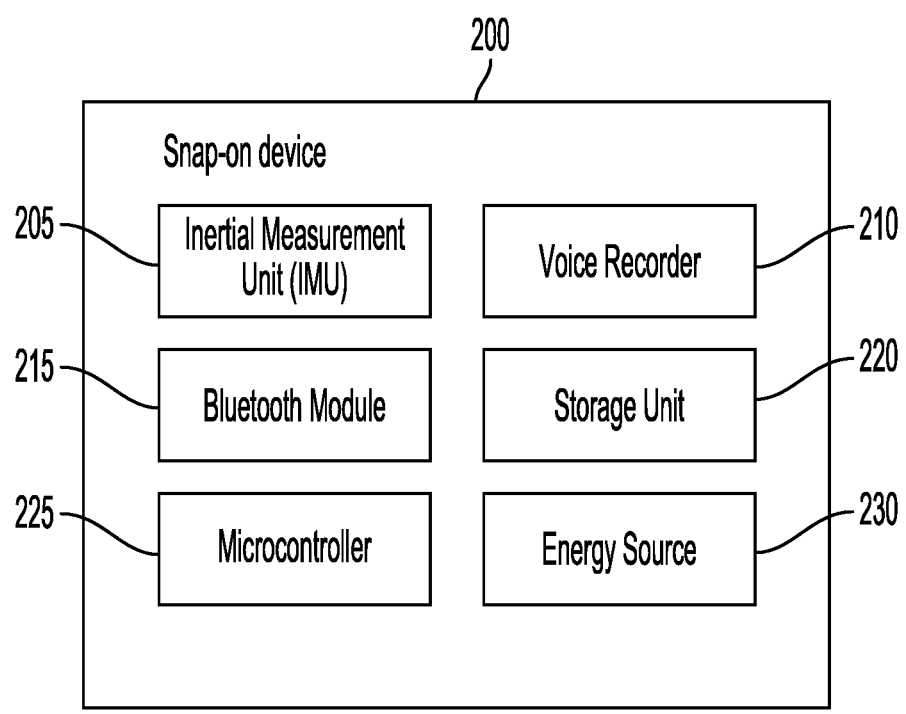
FIG. 2 illustrates an example snap-on device, according to certain example embodiments.

FIG. 2 illustrates an example snap-on device, according to certain example embodiments. As illustrated FIG. 2, the snap-on device 200 (i.e., sensory module) may include an internal measurement unit (IMU) 205, a voice recorder 210, a Bluetooth module 215, a storage unit 220, a microcontroller 225, and an energy source 230. According to certain example embodiments, the IMU 205 may record the child's movements and the objects around the child depending on the placement of the snap-on device 200 in the environment. The voice recorder 210 may be configured to store the auditory sounds from the child (e.g., screams, speaking, etc.) that may be used for further analysis. For example, the stored auditory sounds may be used to access the quality of a given audio sample based on a signal-to-noise ratio (SNR), followed by using machine learning (ML) techniques to identify if a segment of a recorded sound/voice corresponds to a challenging behavior or to forecast/predict challenging behavior. The Bluetooth module 215 may be configured to establish a connection between the snap-on device 200 and an MDU. Further, the storage unit 220 may be configured to store the collected data from the IMU 205 and the voice recorder 210. Additionally, the microcontroller 225 (i.e., processor), may be configured to coordinate between units of the snap-on device 200 and the wearable device. The snap-on device 200 may also include an energy source 230 (e.g., battery, or external power source) to provide the snap-on device 200 with sufficient power to function.

According to certain example embodiments, the MDU may receive the data acquired by the different snap-on devices 200 placed within the environment (i.e., room) or surrounding of the child and from the wearable device that may be worn by the child. Furthermore, the MDU may store backup copies of the acquired data from the snap-on devices 200, perform the analysis, transmit the acquired data and results of the analysis to the cloud, and notify the parents or caregivers of the child in case of detecting an occurrence of challenging behaviors.

Figure 3:
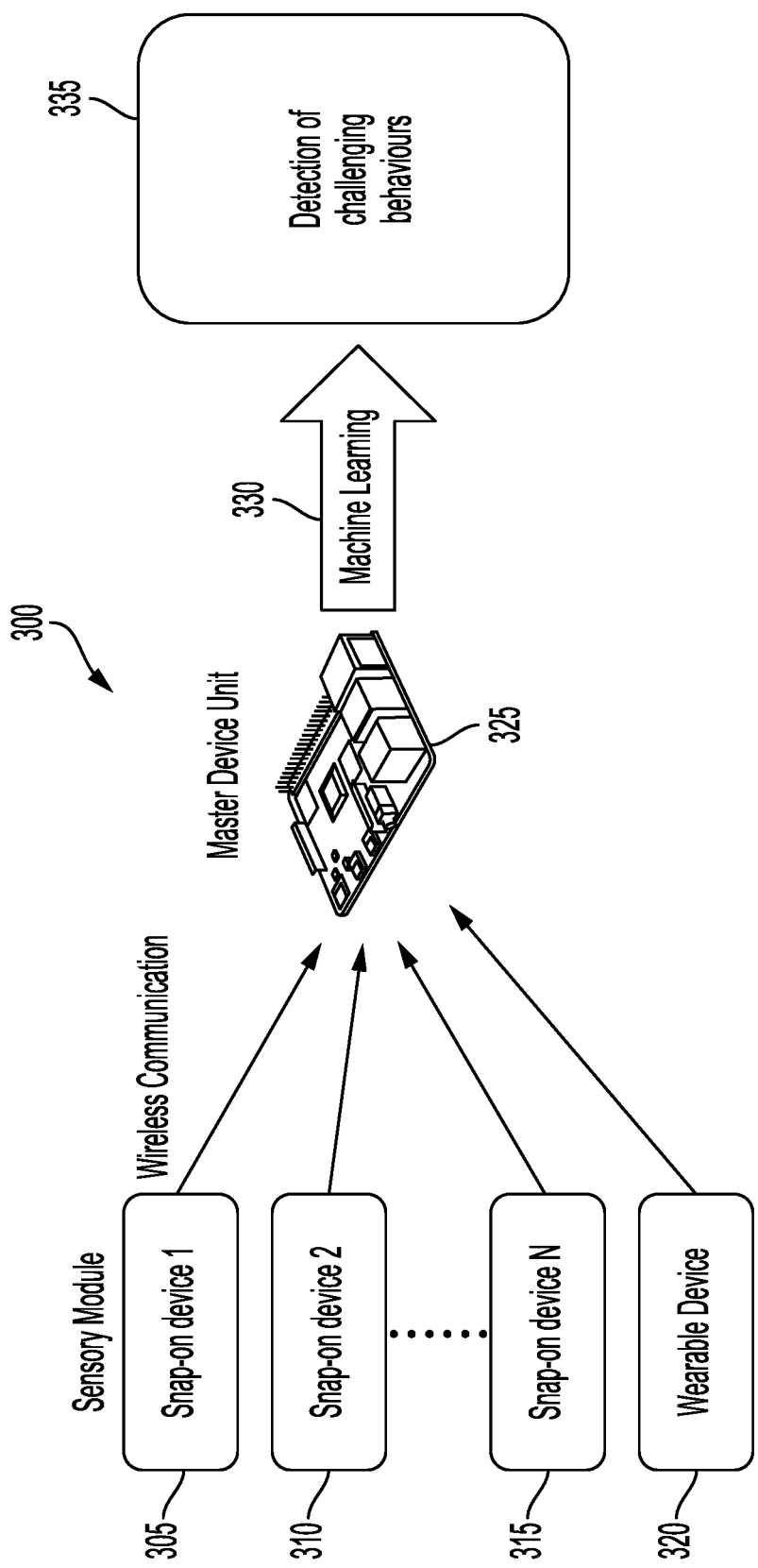
FIG. 3 illustrates an example network connected configuration, according to certain example embodiments.

FIG. 3 illustrates an example network connected configuration, according to certain example embodiments. For instance, in certain example embodiments, the MDU, snap-on devices 200, and the wearable device may constitute a connected network 300 of Internet of Things (IoT). As illustrated in FIG. 3, the network may include one or more snap-on devices 305, 310, 315, and a wearable device 320. Each of the snap-on devices 305, 310, 315 and wearable device 320 may be wirelessly connected to the MDU 325. In certain example embodiments, the wearable device 320 may be placed in various locations of the child such as, for example, the wrist, feet, chest, thigh, ankle, or arm.

As further illustrated in FIG. 3, the MDU 325 may implement one or more ML algorithms 330 using the data obtained by the snap-on devices 305, 310, 315 and wearable device 320 as input data. As a result of implementing the ML algorithm 330, the MDU 325 may determine/detect 335 the presence of challenging behaviors exhibited by the child (i.e., whether the child is exhibiting challenging behavior).

Figure 4A:
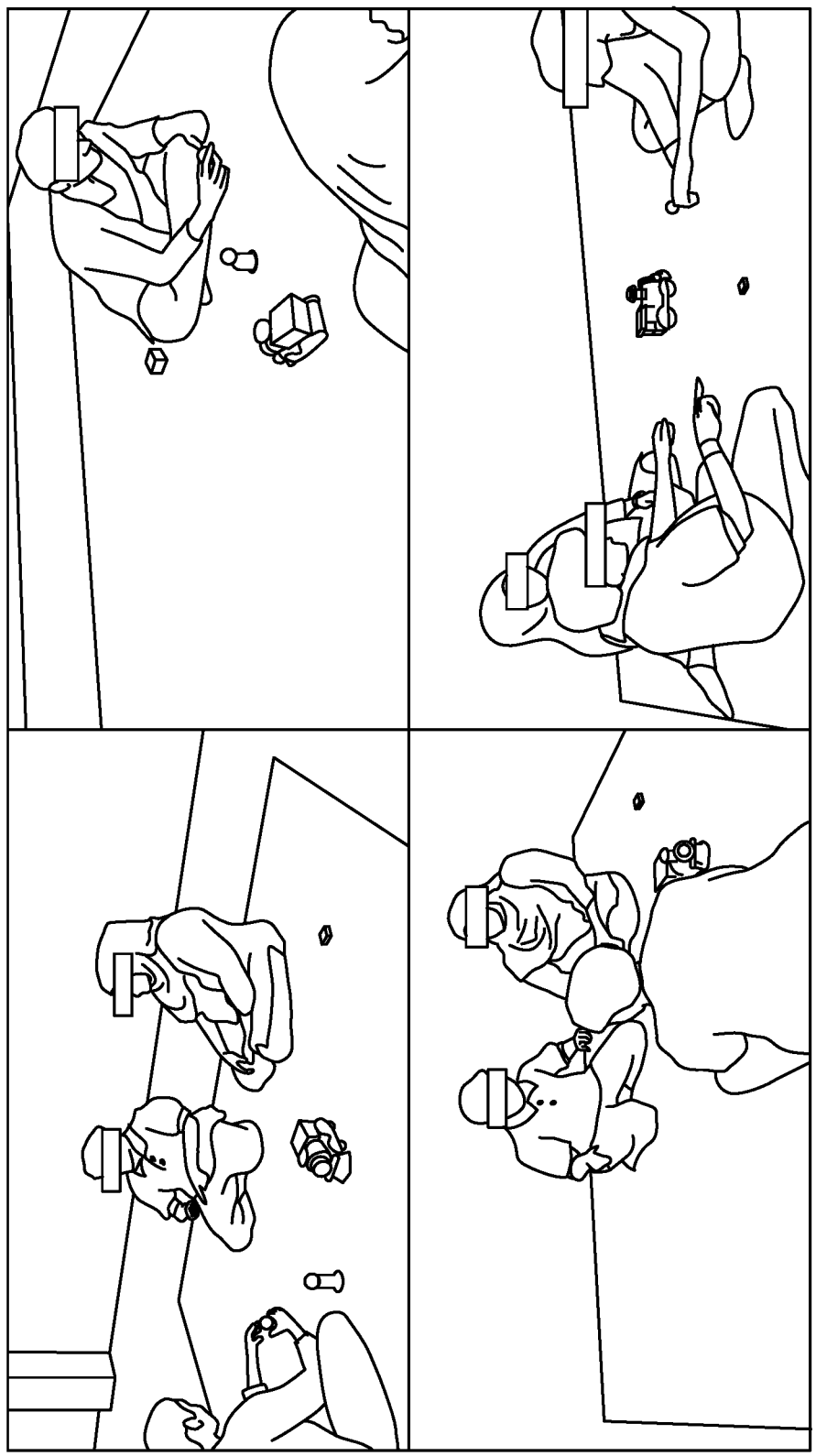
FIG. 4(a) an example video session, according to certain example embodiments.
Figure 4B:
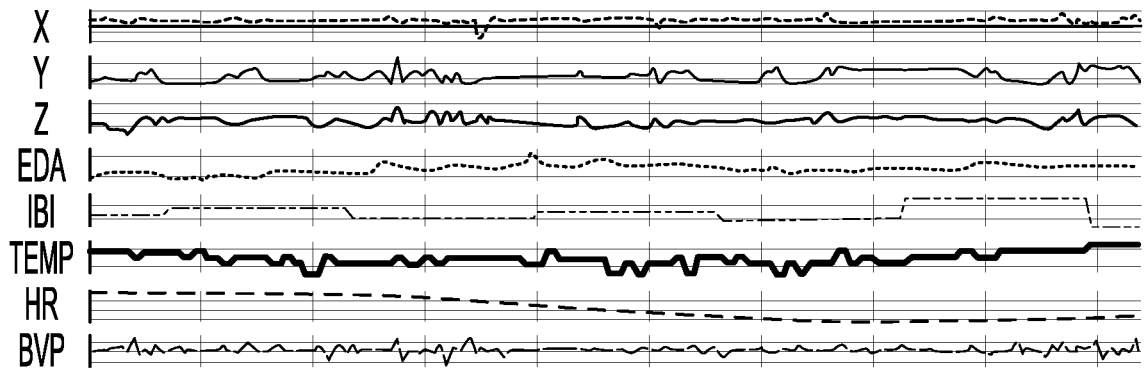
FIG. 4(b) illustrates an example of a set of acquired data signals, according to certain example embodiments.
Figure 4C:
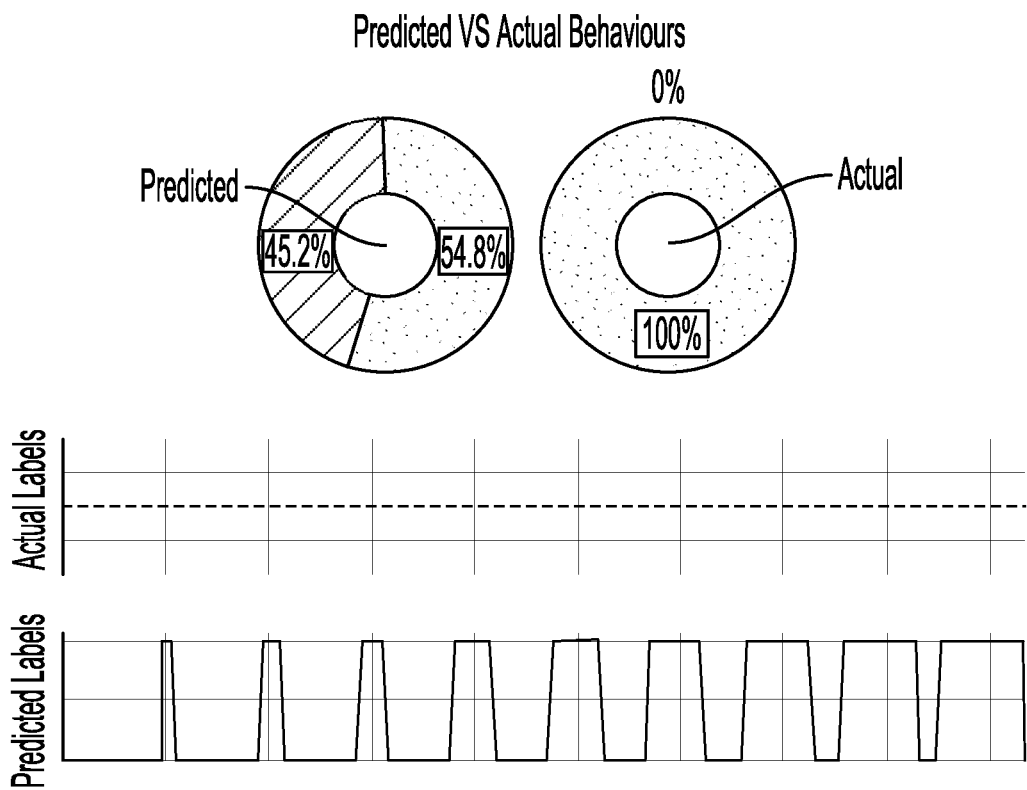
FIG. 4(c) illustrates an example prediction of challenging behavior, according to certain example embodiments.

In certain example embodiments, after acquiring the data from the snap-on devices and/or wearable device, the data signals and physiological changes of the acquired data may be visualized and analyzed by the MDU. For example, the MDU may perform the analysis, and determine the ML predictions for challenging behaviors. In certain example embodiments, the data may be visualized and analyzed via an annotation tool that may make use of such data to create annotated video sessions and ML predictions for challenging behaviors. In some example embodiments, the annotation tool may be implemented on a computer or be incorporated into the MDU to provide visualization, if needed. Alternatively, the annotation tool may be run remotely. For instance, FIG. 4(*a*) illustrates an example video session, according to certain example embodiments. Further, FIG. 4(*b*) illustrates an example of a set of acquired data signals, according to certain example embodiments, and FIG. 4(*c*) illustrates an example prediction of challenging behavior, according to certain example embodiments. In certain example embodiments, the prediction may be used to classify current actions and forecast/predict future instances of challenging behavior. Further, as illustrated in FIG. 4(*c*), the actual behaviors are the true labels or classes as identified by a trained expert (e.g., human), while the predicted label is classified by the ML model. As illustrated in FIGS. 4(*a*)-4(*c*), the annotation tool may be used to display a video session of one or more children being monitored. The annotation tool may also use the data from the snap-on devices and wearable device to display the acquired physiological signals of the monitored children, and a comparison between predicted and actual behaviors.

Figure 5:
FIG. 5 illustrates an example interaction with a social robot, according to certain example embodiments.

FIG. 5 illustrates an example interaction with a social robot, according to certain example embodiments. For instance, in certain example embodiments, the snap-on device and/or the wearable device may be in wireless connection with a social robot 500. The social robot 500 may be configured to respond to an unwanted interaction. For example, as illustrated in FIG. 5, when there is no interaction, the social robot 500 does not execute a response. However, when there is an interaction with, for example, a control device 505 (or any other item in an environment/surrounding of the social robot 500), the social robot 500 may execute a response. The control device may correspond to a snap-on device and MDU. In the example of FIG. 5, the MDU may be equipped with sensors that may be used to act as a snap-on device. In some example embodiments, the response may include the social robot 500 pointing its hand at the control device. In other example embodiments, the social robot 500 may point to the control device and perform an auditory response indicating that the control device 505 should not be picked up. However, in certain example embodiments, the social robot 500 may perform other auditory responses depending on the type of interaction performed with the control device. For instance, the social robot 500 may have normal interactions, for example, by conversing with a human (e.g., child).

Figure 6:
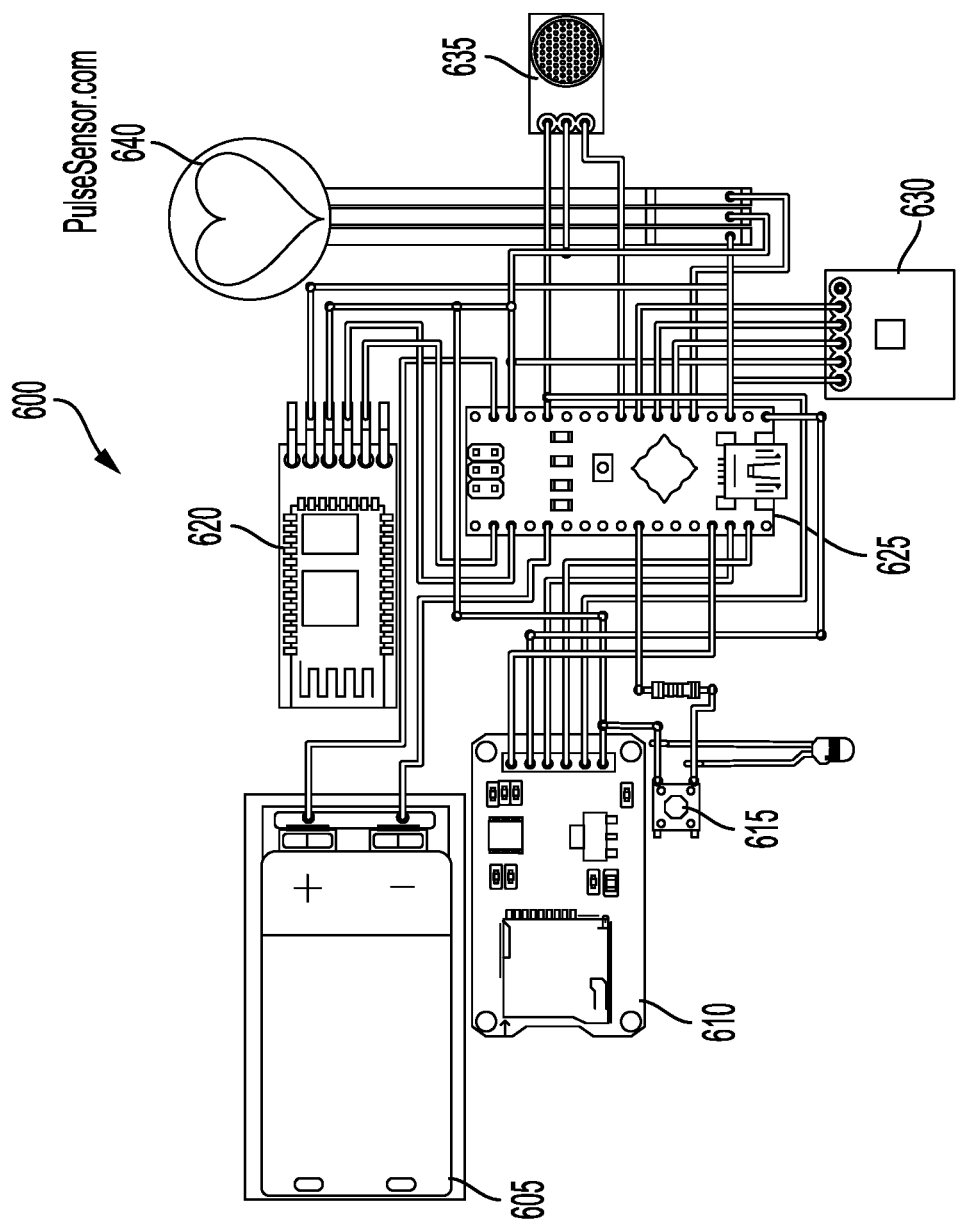
FIG. 6 illustrates an example circuit of a wearable device, according to certain example embodiments.

FIG. 6 illustrates an example circuit of the wearable device 600, according to certain example embodiments. As illustrated in FIG. 6, the circuit may include an accelerometer 630, microphone module 635, microcontroller 625, and Bluetooth module 620. The wearable device 600 may include an Arduino Nano microcontroller 625 that receives inputs and outputs from connected components. The wearable device 600 may also include three sensors, but is not limited to three sensors and may include more or less sensors. The first sensor may be a heart rate sensor 640, which records the subject's heart rate. The second sensor may include an electret microphone 635, which records the sounds the subject is producing along with their environment. The final and third sensor may include a triple axis accelerometer 630, which records the subject's motion in the X, Y, and Z directions. The wearable device 600 also includes an onboard SD card reader 610, which stores all obtained readings on an SD card while the full-duplex HC-05 Bluetooth module 620 transmits the obtained data live to a device(s), such as a computer, for processing. The wearable device 600 also includes a push-button 615, which starts and makes the sensors start record. The entire system 600 may be powered by a 9V battery 605.

Figure 7B:
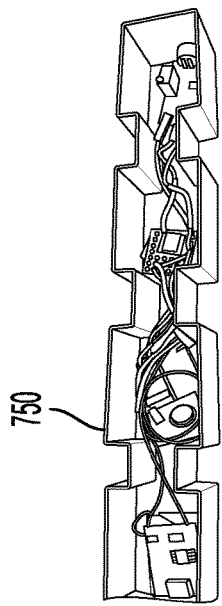
FIG. 7(b) illustrates an example hardware construction of the snap-on device, according to certain example embodiments.
Figure 7C:
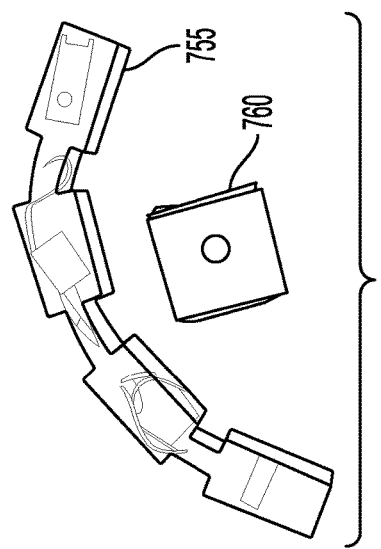
FIG. 7(c) illustrates an example assembled snap-on device, according to certain example embodiments.
Figure 7A:
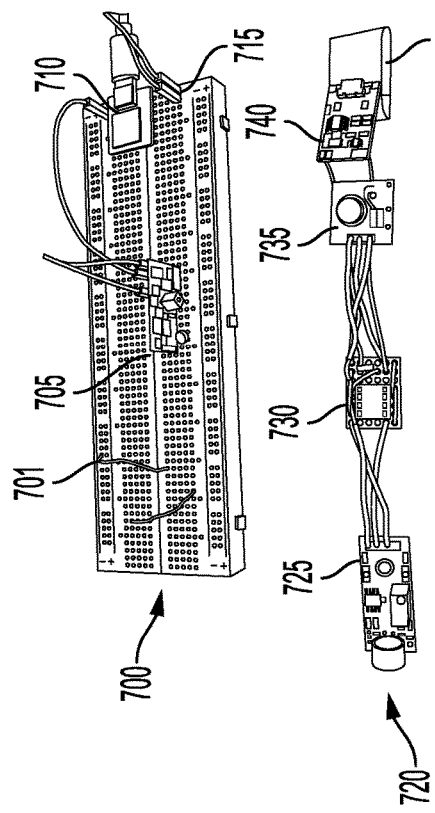
FIG. 7(a) illustrates an example of an electronic circuit and snap-on device, according to certain example embodiments.

FIG. 7(a) illustrates an example of an electronic circuit 700 and snap-on device 720, according to certain example embodiments. FIG. 7(b) illustrates an example hardware construction of the snap-on device, according to certain example embodiments. Further, FIG. 7(c) illustrates an example assembled snap-on device, according to certain example embodiments. As illustrated in FIG. 7(a), the electronic circuit development and testing 700, and snap-on device 720 show a breadboard 701, receiver 705, microcontroller 710, jumper wires 715, voice recorder 725, accelerometer 730, transmitter 735, microcontroller 740, and battery 745. Further, FIG. 7(b) illustrates an example hardware construction in an enclosure 750, and FIG. 7(c) illustrates final prototypes embodied in a soft material 755 (e.g., soft foam-like wrap) and inside a soft small box 760.

Figure 8:
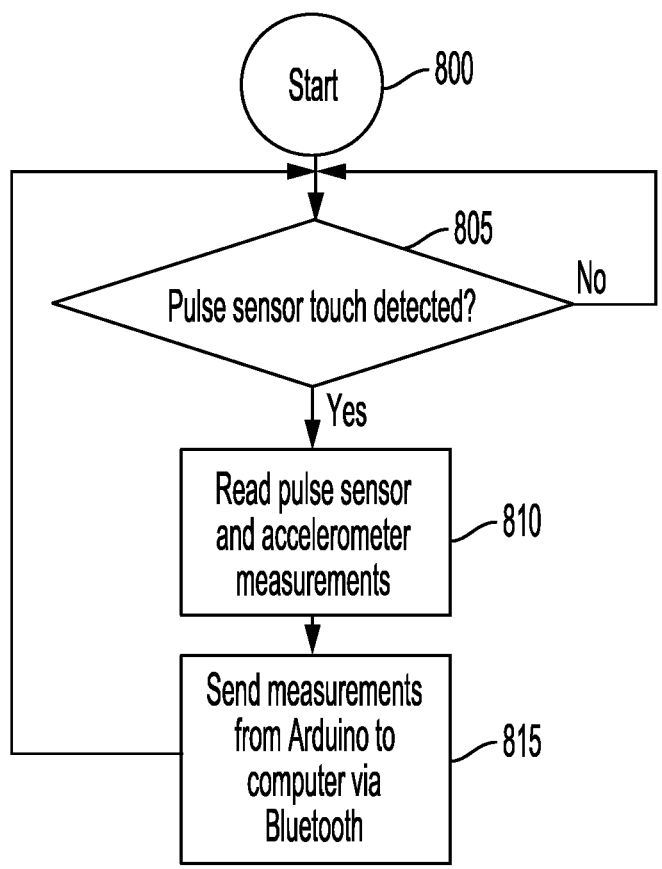
FIG. 8 illustrates an example flow diagram of an operation of the snap-on device, according to certain example embodiments.

FIG. 8 illustrates an example flow diagram of an operation of the snap-on device, according to certain example embodiments. As illustrated FIG. 8, at 800, operation of the snap-on device may begin. At 805, the snap-on device may determine whether a pulse sensor touch has been detected. In some example embodiments, the pulse sensor touch may correspond to a heart rate sensor, and it may be part of the snap-on device. If a pulse sensor touch is not detected, the snap-on device may continue to operate to detect the pulse sensor touch. On the other hand, if it is determined that a pulse sensor touch has been detected, the snap-on device may, at 810, read the pulse sensor and accelerometer measurements. At 815, the snap-on device may send measurements from an Arduino of the snap-on device to a computer (e.g., MDU) via Bluetooth.

Experimental Verification with a Wearable Device

A. Participants

According to certain example embodiments, five male children with autism participated in an experimental verification of the wearable device. The participants were in the age range of between 7 and 10 years old, sessions were conducted with each child individually under the supervision and assistance of a teacher or caregiver. The procedures for this experiment did not include invasive or potentially hazardous methods, and were in accordance with the Code of Ethics of the World Medical Association (Declaration of Helsinki).

Figure 9:
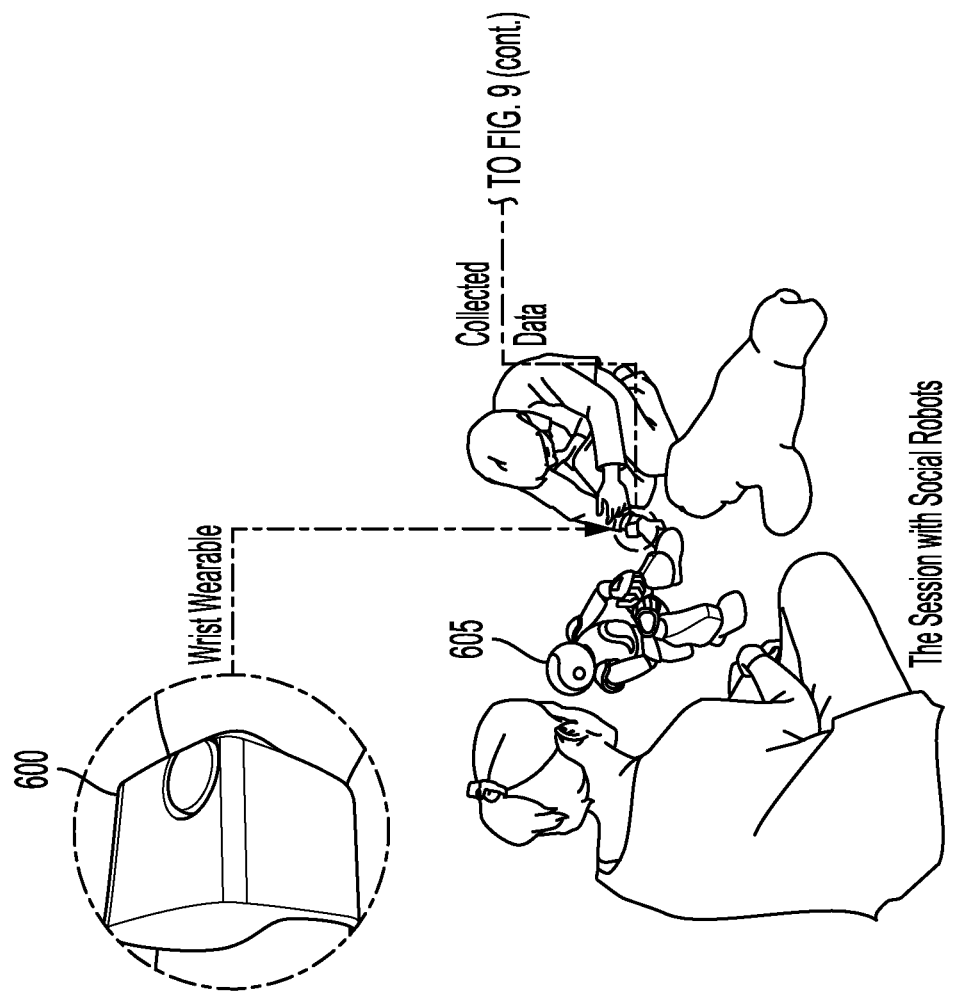
FIG. 9 illustrates an example overview of the adopted methodology in an experiment, according to certain example embodiments.
Figure 9:
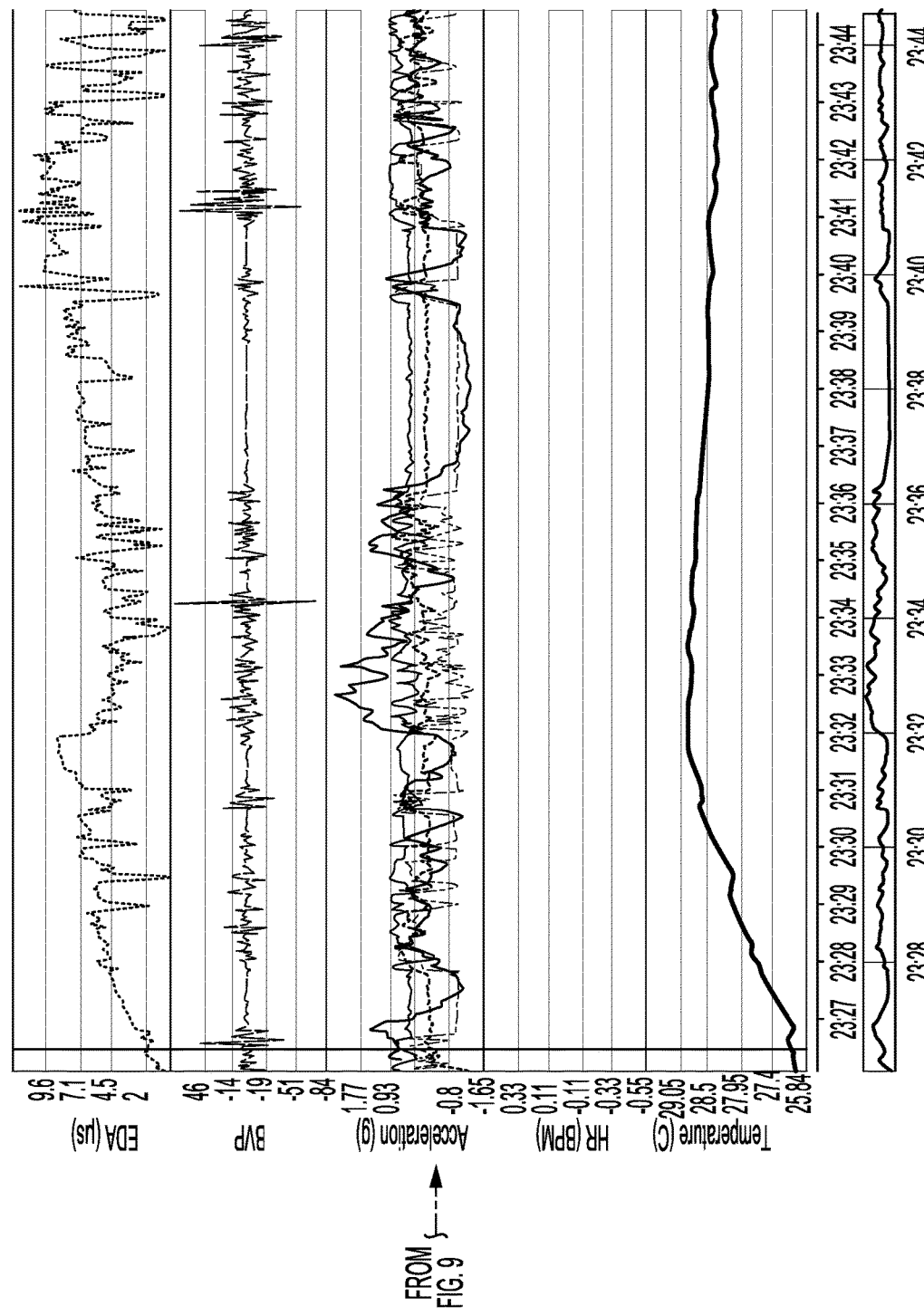

FIG. 9 illustrates an example overview of the adopted methodology in this experiment, according to certain example embodiments. As illustrated in FIG. 9, the children may each be wearing a wearable device 900 on their wrist, and the children may interact with a social robot(s) 905. The wearable device 900 may include a real-time clock, and may be capable of recording physiological data signals of the wearer (e.g., child), and storing the signals in an internal memory of the wearable device 900. During the experiment, data was collected from the wearable device 900 and mapped to a graphical representation 910, as illustrated in FIG. 9.

According to certain example embodiments, the physiological data acquired by the wearable device 900 may include, but not limited to, for example, acceleration (ACC), electrodermal activity (EDA), inter-beat interval (IBI), temperature (TEMP), heart rate (HR), and blood volume pulse (BVP). With ML techniques, it may be possible to determine the instances of challenging behaviors based on the physiological data.

B. Stimuli

According to certain example embodiments, social robots and regular children's toys may be used as stimuli in the study. The social robots may be any type of robot (e.g., interactive robot), and the toys may include, but not limited to, for example, a plush ball (e.g., green rubber ball), a multi-color train, brass cymbals, and/or wooden letter blocks that are placed on a toy truck.

C. Algorithms

Once data has been acquired from the wearable device 900, the data my serve as input into an ML algorithm implemented by the MDU. For instance, in certain example embodiments, the ML algorithm may include a support-vector machine (SVM), a multilayer perceptron (MLP), a decision tree (DT), or an extreme gradient boosting (XGBoost). The SVM may be a non-probabilistic binary linear supervised learning model that may solve and classify both linear and non-linear problems. The MLP may be a learning technique inspired by the biological brain that may include layers of artificial neurons that may learn from data. Further, the DT may be an algorithm that predicts the output by moving through the different discrete decision options that are represented in a tree-like structure until a conclusion is reached. Additionally, the XGBoost may be an ensemble supervised machine learning technique that utilizes regularized gradient boosted decision trees to improve performance and classification speed.

According to certain example embodiments, the input of the ML algorithm (e.g., XGBoost) may include a training data set $\{(x_i, y_i)\}_{i=1}^{N}$, a differentiable loss function $L(y, F(x))$, a number of weak learner (trees) M, and a learning rate a.

In the algorithm, the model may be initialized with a constant value:

$$\widehat{f_{(0)}}(x) = \operatorname{argmin}_\theta \sum_{i=1}^{N} L(y_i, \theta), \tag{1}$$

where arg min is the argument of the minimum θ value, and $\widehat{f_{(0)}}(x)$ is the initial output.

For m=1 to M, the 'gradients' and 'hessians' may be computed as follows:

$$\widehat{g_m}(x_i) = \left[\frac{\partial L(y_i, f(x_i))}{\partial f(x_i)}\right]_{f(x) = \hat{f}_{(m-1)}(x)} \tag{3}$$

$$\widehat{h_m}(x_i) = \left[\frac{\partial^2 L(y_i, f(x_i))}{\partial f(x_i)^2}\right]_{f(x) = \hat{f}_{(m-1)}(x)}. \tag{4}$$

A base learner (e.g., tree) may be fit using the training set:

$$\left\{x_i, -\frac{\hat{g}_m(x_i)}{\hat{h}_m(x_i)}\right\}_{i=1}^{N}, \tag{5}$$

by solving the optimization problem below:

$$\hat{\phi}_m = \operatorname*{argmin}_{\phi \in \Phi} \sum_{i=1}^{N} \frac{1}{2} \hat{h}_m(x_i) \left[ -\frac{\hat{g}_m(x_i)}{\hat{h}_m(x_i)} - \phi(x_i) \right]^2 \quad (6)$$

$$\hat{f}_m(x) = \alpha \hat{\phi}_m(x).$$

In equation (6), $\hat{f}_m(x)$ may represent the model corresponding to the current base learner m, and α may correspond to the learning rate.

Once the base learner is fit using the training set above, the model may be updated with the following model:

$$\hat{f}_{(m)}(x) = \hat{f}_{(m-1)}(x) + \hat{f}_m(x) \quad (7)$$

Finally, the output of the final model may be:

$$\hat{f}(x) = \hat{f}_{(M)}(x) = \sum_{m=0}^{M} \hat{f}_m(x). \quad (8)$$

D. Procedures

Manual annotation was carried out for each of the five children's behaviors. This was done with the help of a free annotation software (BORIS, v. 7.10.2, Torino, Italy). The behaviors were annotated as either 'challenging' or 'non-challenging'. A challenging behavior may be considered to be for example, but not limited to, any action that is interfering, repetitive, stimming, and might inflict harm on oneself or others. Challenging behaviors may also include head banging, arm flapping, ear pulling, kicking, and scratching.

The acquired data from the wearable device 900 was processed. To ensure consistency, the data acquired from the wearable device 900 were preprocessed, and the sampling frequency of every acquired data signal was set to 64 Hz since the different sensors (e.g., wearable device) may obtain data at different sampling rates. According to certain example embodiments, the preprocessing stage included removal of outliers and resampling the training data to ensure that classes are equally balanced. A portion equal to thirty percent of the original dataset was used as the unseen testing set. Initial experiments with the dataset indicated that the extracted features produced better performance when compared to the raw features alone. Thus, only time-domain extracted features (i.e., mean, standard deviation, min, and max) were considered throughout this study.

E. Results

Four ML algorithms were evaluated based on the evaluation metrics in addition to the prediction speed (Table 1). In the results, challenging behaviors were considered to be the positive class. The models were developed using Python libraries (i.e., Sklearn and XGBoost). The depth of the DT algorithm was set to dynamic, and the Gini function was used for the splitting criteria. SVM used a radial basis function kernel with a regularization parameter of 0.1 and a gamma parameter was set to scale. As for the MLP, it contained one hidden layer that consisted of 100 neurons with weights adjusted using stochastic gradient descent at 0.0001 L2 regularization. XGBoost was trained with logistic objective, max depth of 6, alpha equal to 1, learning rate of 0.3, and 100 estimators.

As shown in Table 1, XGBoost showed better overall performance compared to other classifiers in terms of precision (0.88), recall (0.99), F1-Score (0.93), and accuracy (0.99). Additionally, XGBoost achieved the fastest time (i.e., 0.24 sec) to predict the test samples. In this example, it may be possible to predict the detection of challenging behavior. Additionally, the test samples or test dataset may be a portion of the main dataset that was not used in the training dataset. As shown in Table 1, the second best performing algorithm was DT followed by MLP. SVM achieved the lowest performance, and took the longest time to predict the test samples, which was around 2.5 seconds. Due to its performance, XGBoost may be considered in other experiments.

TABLE 1

Evaluation metric scores for four ML algorithms and their test times (in seconds) needed to evaluate the test samples

|         | Precision | Recal | F1-Score | Accuracy | Testing Time |
|---------|-----------|-------|----------|----------|--------------|
| XGBoost | 0.88      | 0.99  | 0.93     | 0.99     | 0.24         |
| MLP     | 0.67      | 0.98  | 0.80     | 0.97     | 0.36         |
| SVM     | 0.24      | 0.91  | 0.38     | 0.85     | 2.48         |
| DT      | 0.87      | 0.92  | 0.89     | 0.98     | 0.29         |

To measure the contribution of each sensor (i.e., of the wearable device 900) to the prediction performance, sensor features were gradually added to the overall feature vector, and the results were compared for the individualized models and combined model (Table 2). As shown in Table 2, with ACC alone (set 1), the classifier performed poorly on all five participants individually and on their combined model. Set 2 considered the effect of adding the HR sensor reading to the feature vector that has led to a large increase in performance for all participants individually and their combined model. As for set 3, adding BVP had little effect on all the models. However, in set 4, adding TEMP slightly improved the performance of the individual personalized models and their combined model. Finally, adding EDA in set 5 led to a further increase in the overall performance for most of the models.

TABLE 2

Results for experiments considering the impact of adding each feature to the feature set for the personalized models of each participant and their combined generalized model

| | Set | | | | | | | | | | | | | | |
|---|---|---|---|---|---|---|---|---|---|---|---|---|---|---|---|
| | 1 | | | 2 | | | 3 | | | 4 | | | 5 | | |
| | Feature | | | | | | | | | | | | | | |
| | ACC | | | Sat 1 + HR | | | Set 2 + BVP | | | Set 3 + TEMP | | | Set 4 + EDA | | |
| Metric | Prec | Recal | F1 | Pre | Recall | F1 | Prec | Recall | F1 | Prec | Recal | F1 | Prec | Recall | F1 |
| Participant 1 | 0.35 | 0.87 | 0.50 | 0.63 | 1 | 0.78 | 0.62 | 1 | 0.77 | 0.79 | 0.97 | 0.87 | 0.79 | 0.97 | 0.87 |
| Participant 2 | 0.53 | 0.89 | 0.67 | 0.72 | 1 | 0.84 | 0.71 | 0.97 | 0.82 | 0.77 | 0.99 | 0.86 | 0.92 | 1 | 0.96 |
| Participant 3 | 0.51 | 0.75 | 0.61 | 0.69 | 0.90 | 0.78 | 0.69 | 0.89 | 0.78 | 0.96 | 0.89 | 0.97 | 0.96 | 0.99 | 0.96 |
| Participant 4 | 0.37 | 0.72 | 0.49 | 0.75 | 0.98 | 0.85 | 0.75 | 0.98 | 0.85 | 1 | 0.98 | 0.99 | 1 | 0.98 | 0.99 |
| Participant 5 | 0.26 | 0.64 | 0.37 | 0.43 | 0.91 | 0.58 | 0.58 | 0.97 | 0.73 | 0.54 | 1 | 0.70 | 0.57 | 1 | 0.73 |
| All Participants | 0.36 | 0.66 | 0.46 | 0.62 | 0.86 | 0.72 | 0.63 | 0.86 | 0.72 | 0.82 | 0.98 | 0.89 | 0.88 | 0.99 | 0.93 |

Figure 10:
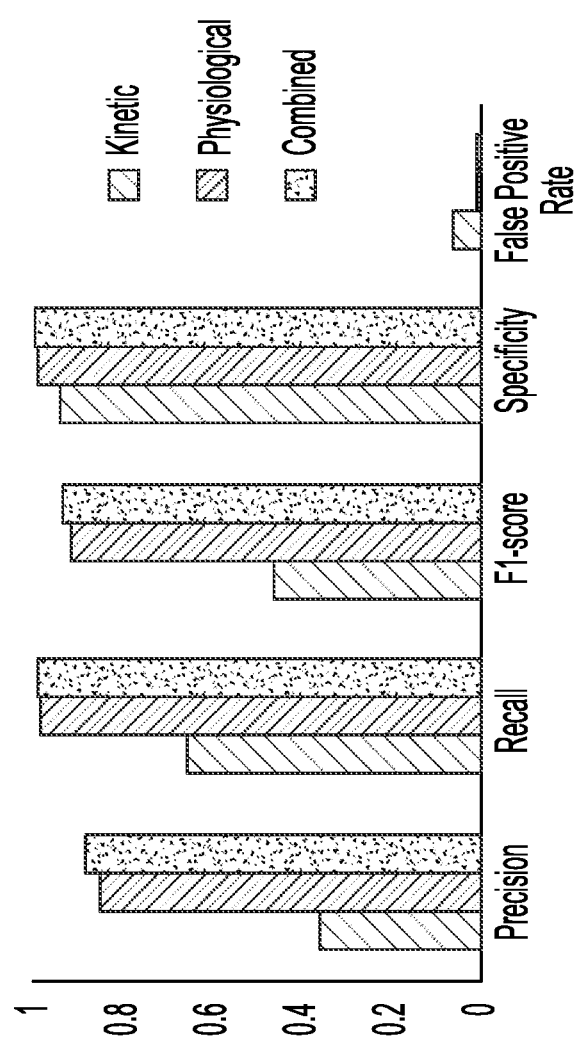
FIG. 10 illustrates an example of evaluation metric results, according to certain example embodiments.

FIG. 10 illustrates an example of evaluation metric results, according to certain example embodiments. For instance, FIG. 10 illustrates the evaluation metrics results for the three categories using the best performing algorithm (i.e., XGBoost). As illustrated in FIG. 10, kinetic, physiological, and a combination of kinetic and physiological features were evaluated, and the evaluation metrics results for the two categories and their combined features are illustrated in FIG. 10. As can be seen from FIG. 10, the results showed that kinetic features alone performed poorly with respect to the physiological and combined features. The physiological features were found to perform similarly to the combined features. In spite of this, the overall best performance came from using the combined features.

Figure 11:
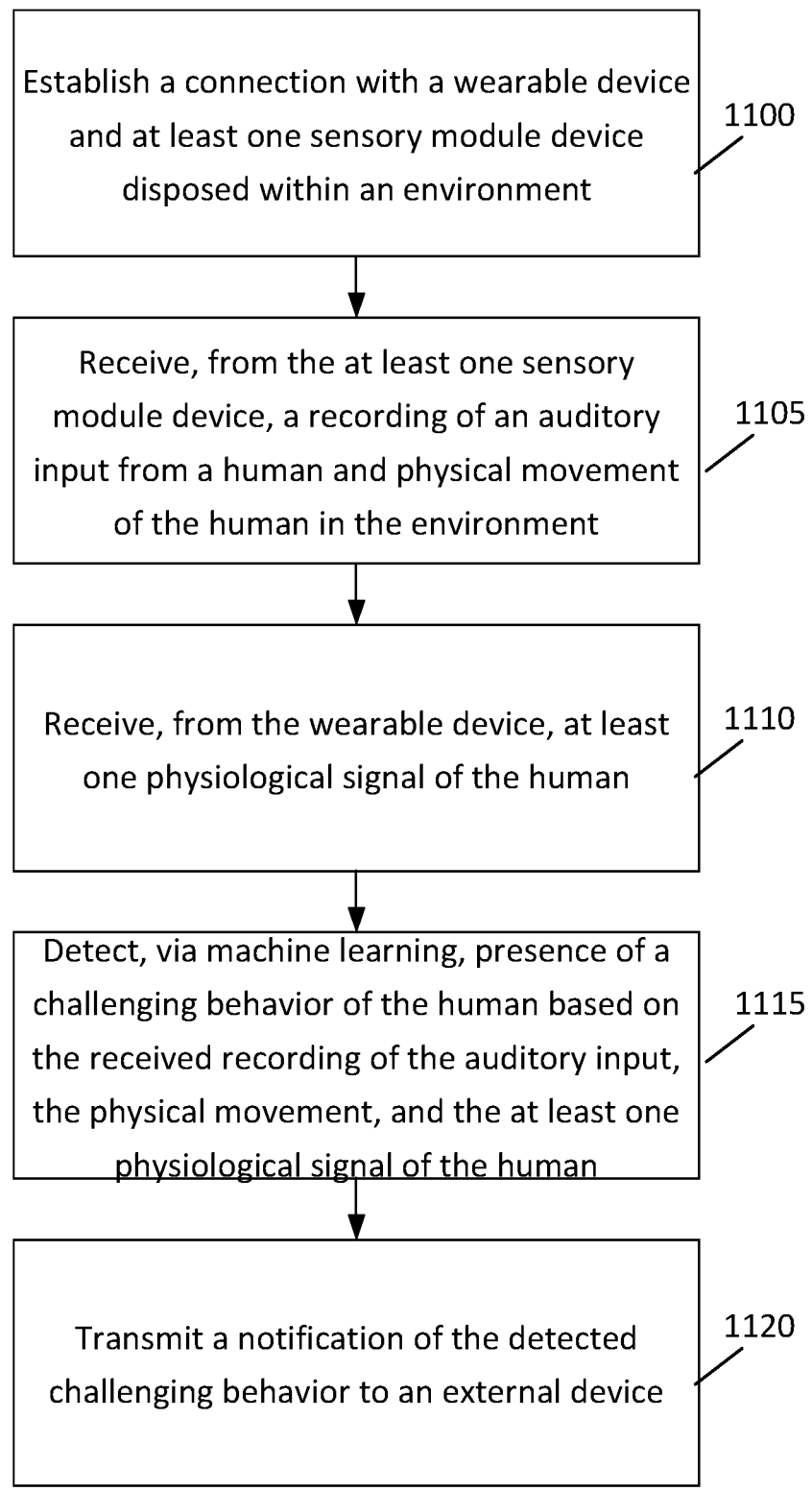
FIG. 11 illustrates an example flow diagram of a method, according to certain example embodiments.

FIG. 11 illustrates an example flow diagram of a method, according to certain example embodiments. In an example embodiment, the method of FIG. 11 may be performed by a computing device. For instance, in an example embodiment, the method of FIG. 11 may be performed by a computer, server, or mobile computing device that may be similar to or included in apparatus 10 illustrated in FIG. 12, and which may correspond to the MDU.

According to certain example embodiments, the method of FIG. 11 may include, at 1100, establishing a connection with a wearable device and at least one sensory module device disposed within an environment. The method may also include, at 1105, receiving, from the at least one sensory module device, a recording of an auditory input from a subject and physical movement of the subject in the environment. The method may further include, at 1110, receiving, from the wearable device, at least one physiological signal of the subject. In addition, the method may include, at 1115, detecting, via machine learning, presence of a challenging behavior of the subject based on the received recording of the auditory input, the physical movement, and the at least one physiological signal of the subject. Further, the method may include, at 1120, transmitting a notification of the detected challenging behavior to an external device.

According to certain example embodiments, the method may also include establishing a connection with a social robot, and controlling the social robot based on the detection of the challenging behavior. According to some example embodiments, the at least one physiological signal comprises at least one of acceleration, electrodermal activity, an inter-beat interval, temperature, heart rate, or blood volume pulse. According to other example embodiments, the challenging behavior may include at least one of an interfering action, a repetitive action, a stimming action, an action of inflicting self-harm or harm to another subject, head banging, arm flapping, ear pulling, kicking, or scratching. According to further example embodiments, the method may also include determining, via the machine learning and based on the least one physiological signal, evaluation metrics. In some example embodiments, the evaluation metrics may include a precision value, a recall value, an F-score value, and an accuracy value.

Figure 12:
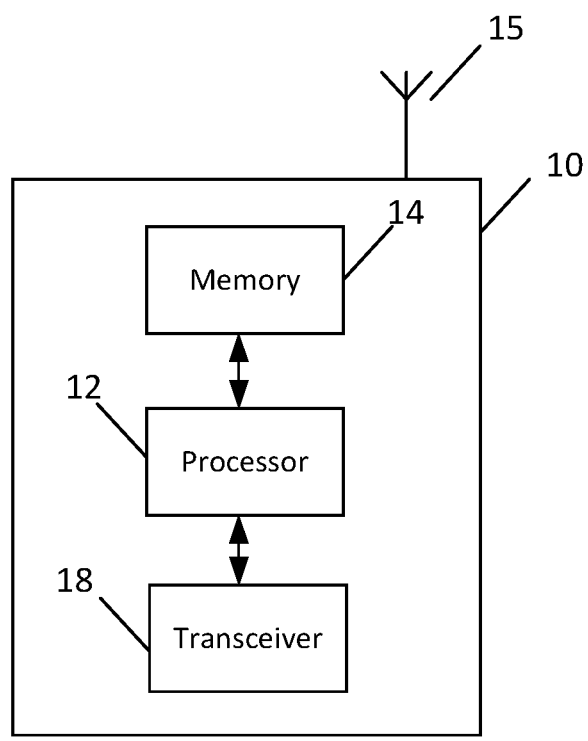
FIG. 12 illustrates an apparatus according to certain example embodiments.

FIG. 12 illustrates an apparatus 10 according to certain example embodiments. In certain example embodiments, apparatus 10 may be a computer, mobile computing device, network device, server, or other similar device. Apparatus 10 may be in communication (i.e., connected to either via wire or wirelessly) with other similar computer devices (e.g., snap-on device and/or wearable device) forming a network of connected computer devices.

In some example embodiments, apparatus 10 may include one or more processors, one or more computer-readable storage medium (for example, memory, storage, or the like), one or more radio access components (for example, a modem, a transceiver, or the like), and/or a user interface.

As illustrated in the example of FIG. 12 apparatus 10 may include or be coupled to a processor 12 for processing information and executing instructions or operations. Processor 12 may be any type of general or specific purpose processor. In fact, processor 12 may include one or more of general-purpose computers, special purpose computers, microprocessors, digital signal processors (DSPs), field-programmable gate arrays (FPGAs), application-specific integrated circuits (ASICs), and processors based on a multi-core processor architecture, as examples. While a single processor 12 is shown in FIG. 12, multiple processors may be utilized according to other example embodiments. For example, it should be understood that, in certain example embodiments, apparatus 10 may include two or more processors that may form a multiprocessor system (e.g., in this case processor 12 may represent a multiprocessor) that may support multiprocessing. According to certain example embodiments, the multiprocessor system may be tightly coupled or loosely coupled (e.g., to form a computer cluster).

Processor 12 may perform functions associated with the operation of apparatus 10 including, as some examples, precoding of antenna gain/phase parameters, encoding and decoding of individual bits forming a communication message, formatting of information, and overall control of the apparatus 10, including processes illustrated in FIGS. 1-11.

Apparatus 10 may further include or be coupled to a memory 14 (internal or external), which may be coupled to processor 12, for storing information and instructions that may be executed by processor 12. Memory 14 may be one or more memories and of any type suitable to the local application environment, and may be implemented using any suitable volatile or nonvolatile data storage technology such as a semiconductor-based memory device, a magnetic memory device and system, an optical memory device and system, fixed memory, and/or removable memory. For example, memory 14 can be comprised of any combination of random access memory (RAM), read only memory (ROM), static storage such as a magnetic or optical disk, hard disk drive (HDD), or any other type of non-transitory machine or computer readable media. The instructions stored in memory 14 may include program instructions or computer program code that, when executed by processor 12, enable the apparatus 10 to perform tasks as described herein.

In certain example embodiments, apparatus 10 may further include or be coupled to (internal or external) a drive or port that is configured to accept and read an external computer readable storage medium, such as an optical disc, USB drive, flash drive, or any other storage medium. For example, the external computer readable storage medium may store a computer program or software for execution by processor 12 and/or apparatus 10 to perform any of the methods illustrated in FIGS. 1-11.

In some example embodiments, apparatus 10 may also include or be coupled to one or more antennas 15 for receiving a downlink signal and for transmitting via an uplink from apparatus 10. Apparatus 10 may further include a transceiver 18 configured to transmit and receive information. The transceiver 18 may also include a radio interface (e.g., a modem) coupled to the antenna 15. The radio interface may include other components, such as filters, converters signal shaping components, and the like, to process symbols, carried by a downlink or an uplink.

For instance, transceiver 18 may be configured to modulate information on to a carrier waveform for transmission by the antenna(s) 15 and demodulate information received via the antenna(s) 15 for further processing by other elements of apparatus 10. In other example embodiments, transceiver 18 may be capable of transmitting and receiving signals or data directly. Additionally or alternatively, in some example embodiments, apparatus 10 may include an input and/or output device (I/O device). In certain example embodiments, apparatus 10 may further include a user interface, such as a graphical user interface or touchscreen.

In certain example embodiments, memory 14 stores software modules that provide functionality when executed by processor 12. The modules may include, for example, an operating system that provides operating system functionality for apparatus 10. The memory may also store one or more functional modules, such as an application or program, to provide additional functionality for apparatus 10. The components of apparatus 10 may be implemented in hardware, or as any suitable combination of hardware and software.

According to certain example embodiments, processor 12 and memory 14 may be included in or may form a part of processing circuitry or control circuitry. In addition, in some example embodiments, transceiver 18 may be included in or may form a part of transceiving circuitry.

As used herein, the term "circuitry" may refer to hardware-only circuitry implementations (e.g., analog and/or digital circuitry), combinations of hardware circuits and software, combinations of analog and/or digital hardware circuits with software/firmware, any portions of hardware processor(s) with software (including digital signal processors) that work together to cause an apparatus (e.g., apparatus 10) to perform various functions, and/or hardware circuit(s) and/or processor(s), or portions thereof, that use software for operation but where the software may not be present when it is not needed for operation. As a further example, as used herein, the term "circuitry" may also cover an implementation of a hardware circuit or processor (or multiple processors), or portion of a hardware circuit or processor, and its accompanying software and/or firmware.

In certain example embodiments, apparatus 10 may be controlled by memory 14 and processor 12 to establish a connection with a wearable device and at least one sensory module device disposed within an environment. Apparatus 10 may also be controlled by memory 14 and processor 12 to receive, from the at least one sensory module device, a recording of an auditory input from a subject and physical movement of the subject in the environment. Apparatus 10 may further be controlled by memory 14 and processor 12 to receive, from the wearable device, at least one physiological signal of the subject. In addition, apparatus 10 may be controlled by memory 14 and processor 12 to detect, via machine learning, presence of a challenging behavior of the subject based on the received recording of the auditory input, the physical movement, and the at least one physiological signal of the subject. Further, apparatus 10 may be controlled by memory 14 and processor 12 to transmit a notification of the detected challenging behavior to an external device.

In some example embodiments, an apparatus (e.g., apparatus 10) may include means for performing a method, a process, or any of the variants discussed herein. Examples of the means may include one or more processors, memory, controllers, transmitters, receivers, sensors, and/or computer program code for causing the performance of the operations.

Certain example embodiments may further be directed to an apparatus that includes means for performing any of the methods described herein including, for example, means for establishing a connection with a wearable device and at least one sensory module device disposed within an environment. The apparatus may also include means for receiving, from the at least one sensory module device, a recording of an auditory input from a subject and physical movement of the subject in the environment. The apparatus may further include means for receiving, from the wearable device, at least one physiological signal of the subject. In addition, the apparatus may include means for detecting, via machine learning, presence of a challenging behavior of the subject based on the received recording of the auditory input, the physical movement, and the at least one physiological signal of the subject. Further, the apparatus may include means for transmitting a notification of the detected challenging behavior to an external device.

Certain example embodiments described herein provide several technical improvements, enhancements, and/or advantages. In some example embodiments, it may be possible to provide a non-obstructive snap-on and/or wearable device. Additionally, the snap-on device may be placed within a room and can be attached to a child's toys, and may also be enclosed with a soft material to improve safety during challenging behaviors.

As described herein, a computer program product may include one or more computer-executable components which, when the program is run, are configured to carry out some example embodiments. The one or more computer-executable components may be at least one software code or portions of it. Modifications and configurations required for implementing functionality of certain example embodiments may be performed as routine(s), which may be implemented as added or updated software routine(s). Software routine(s) may be downloaded into the apparatus.

As an example, software or a computer program code or portions of code may be in a source code form, object code form, or in some intermediate form, and may be stored in some sort of carrier, distribution medium, or computer readable medium, which may be any entity or device capable of carrying the program. Such carriers may include a record medium, computer memory, read-only memory, photoelectrical and/or electrical carrier signal, telecommunications signal, and software distribution package, for example. Depending on the processing power needed, the computer program may be executed in a single electronic digital computer or it may be distributed amongst a number of computers. The computer readable medium or computer readable storage medium may be a non-transitory medium.

In other example embodiments, the functionality may be performed by hardware or circuitry included in an apparatus (e.g., apparatus 10), for example through the use of an application specific integrated circuit (ASIC), a programmable gate array (PGA), a field programmable gate array (FPGA), or any other combination of hardware and software. In yet another example embodiment, the functionality may be implemented as a signal, a non-tangible means that can be carried by an electromagnetic signal downloaded from the Internet or other network.

According to certain example embodiments, an apparatus, such as a node, device, or a corresponding component, may be configured as circuitry, a computer or a microprocessor, such as single-chip computer element, or as a chipset, including at least a memory for providing storage capacity used for arithmetic operation and an operation processor for executing the arithmetic operation.

One having ordinary skill in the art will readily understand that the invention as discussed above may be practiced with steps in a different order, and/or with hardware elements in configurations which are different than those which are disclosed. Therefore, although the invention has been described based upon these example embodiments, it would be apparent to those of skill in the art that certain modifications, variations, and alternative constructions would be apparent, while remaining within the spirit and scope of example embodiments.

Partial Glossary

DT Decision Tree
MDU Master Device Unit
ML Machine Learning
MLP Multilayer Perceptron
SVM Support-Vector Machine
XGBoost Extreme Gradient Boosting

We claim:

1. A method performed by a master device unit for detecting challenging behaviors, comprising:
  establishing a connection with a wearable device and at least one sensory module device disposed within an environment;
  receiving, from the at least one sensory module device, a recording of an auditory input from a subject and physical movement of the subject in the environment;
  receiving, from the wearable device, at least one physiological signal of the subject;
  detecting, via machine learning, presence of a challenging behavior of the subject based on the received recording of the auditory input, the physical movement, and the at least one physiological signal of the subject;
  transmitting a notification of the detected challenging behavior to an external device;
  establishing a connection with a social robot; and
  controlling the social robot to perform an auditory response that identifies the master device unit, or that is based on a type of interaction performed with the master device unit.

2. The method according to claim 1, wherein the at least one physiological signal comprises at least one of the following:
  acceleration,
  electrodermal activity,
  an inter-beat interval,
  temperature,
  heart rate, or
  blood volume pulse.

3. The method according to claim 1, wherein the challenging behavior comprises at least one of the following:
  an interfering action,
  a repetitive action,
  a stimming action,
  an action of inflicting self-harm or harm to another subject,
  head banging,
  arm flapping,
  ear pulling,
  kicking, or
  scratching.

4. The method according to claim 1, further comprising:
  determining, via the machine learning and based on the least one physiological signal, evaluation metrics,
  wherein the evaluation metrics comprises a precision value, a recall value, an F-score value, and an accuracy value.

5. An apparatus, comprising:
  at least one processor; and
  at least one memory comprising computer program code,
  wherein the at least one memory and the computer program code are configured to, with the at least one processor, cause the apparatus at least to:
  establish a connection with a wearable device and at least one sensory module device disposed within an environment;
  receive, from the at least one sensory module device, a recording of an auditory input from a subject and physical movement of the subject in the environment;
  receive, from the wearable device, at least one physiological signal of the subject;
  detect, via machine learning, presence of a challenging behavior of the subject based on the received recording of the auditory input, the physical movement, and the at least one physiological signal of the subject;
  transmit a notification of the detected challenging behavior to an external device;
  establish a connection with a social robot; and
  control the social robot to perform an auditory response that identifies the apparatus, or that is based on a type of interaction performed with the apparatus.

6. The apparatus according to claim 5, wherein the at least one physiological signal comprises at least one of the following:
acceleration,
electrodermal activity,
an inter-beat interval,
temperature,
heart rate, or
blood volume pulse.

7. The apparatus according to claim 5, wherein the challenging behavior comprises at least one of the following:
an interfering action,
a repetitive action,
a stimming action,
an action of inflicting self-harm or harm to another subject,
head banging,
arm flapping,
ear pulling,
kicking, or
scratching.

8. The apparatus according to claim 5, wherein the apparatus is further caused to:
determine, via the machine learning and based on the least one physiological signal, evaluation metrics,
wherein the evaluation metrics comprises a precision value, a recall value, an F-score value, and an accuracy value.

9. A non-transitory computer readable medium comprising computer executable code which, when executed by a processor of a master device unit, causes the processor to:
establish a connection with a wearable device and at least one sensory module device disposed within an environment;
receive, from the at least one sensory module device, a recording of an auditory input from a subject and physical movement of the subject in the environment;
receive, from the wearable device, at least one physiological signal of the subject;
detect, via machine learning, presence of a challenging behavior of the subject based on the received recording of the auditory input, the physical movement, and the at least one physiological signal of the subject;
transmit a notification of the detected challenging behavior to an external device;
establish a connection with a social robot; and
control the social robot to perform an auditory response that identifies the master device unit, or that is based on a type of interaction performed with the master device unit.

10. The non-transitory computer readable medium according to claim 9, wherein the at least one physiological signal comprises at least one of the following:
acceleration,
electrodermal activity,
an inter-beat interval,
temperature,
heart rate, or
blood volume pulse.

11. The non-transitory computer readable medium according to claim 9, wherein the challenging behavior comprises at least one of the following:
an interfering action,
a repetitive action,
a stimming action,
an action of inflicting self-harm or harm to another subject,
head banging,
arm flapping,
ear pulling,
kicking, or
scratching.

12. The non-transitory computer readable medium according to claim 9, wherein the processor is further caused to:
determine, via the machine learning and based on the least one physiological signal, evaluation metrics,
wherein the evaluation metrics comprises a precision value, a recall value, an F-score value, and an accuracy value.

* * * * *